United States Patent
Murayama et al.

(10) Patent No.: US 9,217,540 B2
(45) Date of Patent: Dec. 22, 2015

(54) DEVICE AND METHOD FOR REMOVING DISSOLVED OXYGEN IN ALCOHOL, ALCOHOL SUPPLY APPARATUS AND RINSING LIQUID SUPPLY APPARATUS

(71) Applicant: ORGANO CORPORATION, Tokyo (JP)

(72) Inventors: Masami Murayama, Tokyo (JP); Hiroshi Sugawara, Tokyo (JP); Kazushige Takahashi, Tokyo (JP)

(73) Assignee: ORGANO CORPORATION, Tokyo (JP)

( * ) Notice: Subject to any disclaimer, the term of this patent is extended or adjusted under 35 U.S.C. 154(b) by 0 days.

(21) Appl. No.: 14/380,148

(22) PCT Filed: Feb. 1, 2013

(86) PCT No.: PCT/JP2013/052339
§ 371 (c)(1),
(2) Date: Aug. 21, 2014

(87) PCT Pub. No.: WO2013/125328
PCT Pub. Date: Aug. 29, 2013

(65) Prior Publication Data
US 2015/0013798 A1     Jan. 15, 2015

(30) Foreign Application Priority Data
Feb. 23, 2012   (JP) .................................. 2012-037379

(51) Int. Cl.
| | |
|---|---|
| *C07C 29/88* | (2006.01) |
| *B01D 11/00* | (2006.01) |
| *F17D 3/00* | (2006.01) |
| *C07C 29/90* | (2006.01) |
| *H01L 21/02* | (2006.01) |
| *B08B 3/00* | (2006.01) |

(52) U.S. Cl.
CPC . *F17D 3/00* (2013.01); *C07C 29/90* (2013.01); *B08B 3/00* (2013.01); *H01L 21/02052* (2013.01); *Y10T 137/87338* (2015.04)

(58) Field of Classification Search
CPC ............ C07C 29/88; C07C 29/90; F17D 3/00
USPC ............... 568/913, 922; 422/261; 137/599.11
See application file for complete search history.

(56) References Cited

U.S. PATENT DOCUMENTS

| | | | |
|---|---|---|---|
| 7,344,649 B2 * | 3/2008 | Redlingshofer et al. ...... 210/757 |
| 2002/0045726 A1 | 4/2002 | Heydenreich et al. | |
| 2005/0230322 A1 | 10/2005 | Redlingshofer et al. | |
| 2010/0160149 A1 | 6/2010 | Barkhordarian et al. | |

FOREIGN PATENT DOCUMENTS

| | | |
|---|---|---|
| CN | 102355952 A | 2/2012 |
| EP | 0145262 | 6/1985 |
| EP | 0441355 | 8/1991 |
| GB | 1228943 | 4/1971 |
| JP | 5879590 | 5/1983 |
| JP | 4-149001 | 5/1992 |
| JP | 05-096283 | 4/1993 |
| JP | 2004-105797 | 4/2004 |
| JP | 2010-142804 | 7/2010 |
| JP | 2010-214321 | 9/2010 |
| WO | 2008/090354 | 7/2008 |

OTHER PUBLICATIONS

Search report from International Bureau of WIPO in PCT/JP2013/052339, mail date is Feb. 26, 2013.
Office Action issued Apr. 1, 2015 in CN 201380010704, and English Translation thereof.
Search Report and Written Opinion issued in Singapore Patent Application No. 11201405128T, dated Sep. 1, 2015.
Partial English-language translation of Office Action issued in a counterpart Korean Patent Application, dated Aug. 27, 2015.

* cited by examiner

*Primary Examiner* — Sikarl Witherspoon
(74) *Attorney, Agent, or Firm* — Greenblum & Bernstein, P.L.C.

(57) ABSTRACT

Dissolved oxygen in alcohol is efficiently removed with a simple configuration. Device for removing dissolved oxygen in alcohol has a hydrogen-occluding metal catalyst in which hydrogen is occluded, the catalyst being charged in a device. Dissolved oxygen is removed from alcohol that contains the dissolved oxygen by bringing the alcohol into contact with the hydrogen-occluding metal catalyst. A method of removing dissolved oxygen in alcohol has removing dissolved oxygen from alcohol that contains the dissolved oxygen by bringing the alcohol into contact with a hydrogen-occluding metal catalyst which occludes hydrogen.

7 Claims, 2 Drawing Sheets

DEVICE AND METHOD FOR REMOVING DISSOLVED OXYGEN IN ALCOHOL, ALCOHOL SUPPLY APPARATUS AND RINSING LIQUID SUPPLY APPARATUS

TECHNICAL FIELD

The present invention relates to a device and a method for removing dissolved oxygen in alcohol. The present invention also relates to an alcohol supply apparatus and a rinsing liquid supply apparatus that use the device.

BACKGROUND ART

When ultrapure water is used in processes for manufacturing semiconductors, the concentration of dissolved oxygen (DO) in the ultrapure water needs to be reduced such that it is, for example, equal to or less than 10 ppb, and even such that it is equal to or less than 1 ppb, by means of vacuum degasifier or membrane degasifier in order to prevent oxidization of the surface of a substrate.

In addition to ultrapure water, many kinds of chemicals are used in semiconductor manufacturing processes. In particular, isopropyl alcohol (IPA) is frequently used as a re-rinsing liquid after rinsing of a substrate and as a drying liquid used in a drying process. At present, the concentration of dissolved oxygen in IPA is not subject to any control. However, as further advances in semiconductor devices occur, in which the devices are configured with finer structures and higher integration, dissolved oxygen in IPA may cause unexpected oxidization of semiconductor devices and lower yields. Hence, the need may arise to remove the amount of dissolved oxygen in IPA to a low concentration level.

Patent Document 1 discloses a method of degassing a chemicals that contains an organic solvent. According to the method, the chemicals is fed to one side of a homogeneous polyolefin film and the other side of the homogeneous film is depressurized, whereby oxygen in the chemicals is removed.

PATENT LITERATURE

Patent Literature 1: JP2004-105797
Patent Literature 2: JP2010-214321

SUMMARY OF THE INVENTION

Problem to be Solved by the Invention

In order to remove the amount of dissolved oxygen to a low concentration level by means of the method disclosed in Patent Literature 1, an increase in the capacity of a vacuum pump or a decrease in the amount of the chemicals to be treated is required. This leads to an increase in the amount of space for installation and an increase in electric power consumption.

The object of the present invention is to provide a device and a method having a simple configuration to remove dissolved oxygen efficiently in alcohol.

Means to Solve the Problem

A device for removing dissolved oxygen in alcohol according to the present invention comprises a hydrogen-occluding metal catalyst in which hydrogen is occluded, the catalyst being charged in the device. The dissolved oxygen is removed from alcohol that contains the dissolved oxygen by bringing the alcohol into contact with the hydrogen-occluding metal catalyst. A method of removing dissolved oxygen in alcohol according to the present invention comprises removing dissolved oxygen from alcohol that contains the dissolved oxygen by bringing the alcohol into contact with a hydrogen-occluding metal catalyst which occludes hydrogen.

Alcohol that contains dissolved oxygen is fed through the hydrogen-occluding metal catalyst in which hydrogen is occluded, whereby the dissolved oxygen in the alcohol and hydrogen occluded in the hydrogen-occluding metal catalyst generate water on the surface of the hydrogen-occluding metal catalyst which occludes hydrogen ($2H_2+O_2 \rightarrow 2H_2O$). Based on this chemical reaction, a simple configuration can be used to remove dissolved oxygen efficiently in alcohol.

Effect of the Invention

Thus, according to the present invention, it is possible to provide a device and a method having a simple configuration to remove dissolved oxygen efficiently in alcohol.

EMBODIMENTS FOR CARRYING OUT THE INVENTION

First Embodiment

Figure 1:
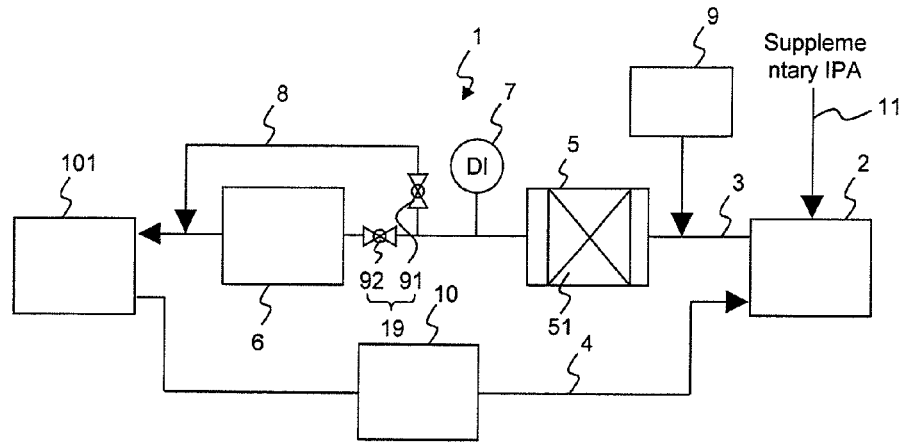
FIG. 1 is a diagram schematically illustrating the arrangement of an alcohol supply apparatus according to a first embodiment of the present invention.

FIG. 1 shows a diagram schematically illustrating the arrangement of an alcohol supply apparatus (IPA supply apparatus 1) according to the first embodiment of the present invention.

IPA supply apparatus 1 according to the embodiment supplies IPA drying liquid, which is used to dry semiconductor devices, to semiconductor device manufacturing apparatus 101. IPA supply apparatus 1 has IPA storage tank 2, IPA supply line 11, IPA supply line 3 and return line 4. IPA storage tank 2 stores IPA. IPA supply line 11 supplies IPA to IPA storage tank 2. IPA supply line 3 supplies the IPA drying liquid to semiconductor device manufacturing apparatus 101. Return line 4 feeds the IPA drying liquid, discharged from semiconductor device manufacturing apparatus 101, back to IPA storage tank 2. IPA supply line 3 is provided with device for removing dissolved oxygen 5 and water removing device 6 positioned downstream thereof. Device for removing dissolved oxygen 5 removes dissolved oxygen in the IPA drying liquid. IPA supply apparatus 1 according to the embodiment has a wide applicability not only for drying of semiconductor devices but also for cases where IPA is used for rinsing or for drying of an object or for both rinsing and drying an object.

Device for removing dissolved oxygen 5 has a housing in which hydrogen-occluding metal catalyst 51 is charged. In the following descriptions, hydrogen-occluding metal catalyst 51 means a hydrogen-occluding metal catalyst in which hydrogen has been already occluded before the IPA drying liquid or rinsing liquid, described later, passes through the hydrogen-occluding metal catalyst. When hydrogen-occluding metal catalyst 51 is charged, a hydrogen-occluding metal catalyst in which hydrogen has been pre-occluded may be placed in the housing. Alternatively, a hydrogen-occluding metal in which hydrogen is not occluded may be placed in the housing, and thereafter hydrogen may be occluded in the hydrogen-occluding metal before the IPA drying liquid or rinsing liquid, described later, passes through the hydrogen-occluding metal. Occlusion takes place by bringing hydrogen gas into contact with the catalyst or by feeding water that contains hydrogen etc. through the catalyst. The occlusion of hydrogen by hydrogen-occluding metal rather easily occurs under pressure and temperature. Hydrogen-occluding metal can also reversibly release hydrogen. A chemical reaction, $2H_2+O_2 \rightarrow 2H_2O$ occurs on the surface of hydrogen-occluding metal catalyst 51 between dissolved oxygen in the IPA drying liquid and hydrogen occluded in hydrogen-occluding metal catalyst 51 by bringing the IPA drying liquid that contains dissolved oxygen into contact with hydrogen-occluding metal catalyst 51. Whereby, at least a part of dissolved oxygen in the IPA drying liquid is removed. Magnesium (Mg), titanium (Ti), vanadium (V), platinum (Pt) and palladium (Pd) may be used as hydrogen-occluding metals, and platinum-group metals are preferably used. In particular, platinum, palladium and an alloy of platinum and palladium are preferable used as hydrogen-occluding metals due to their high catalyst activity.

Hydrogen-occluding metal catalyst 51 preferably has a carrier, such as activated carbon and ion exchange resin, and hydrogen-occluding metal carried on the carrier, but is not limited to this. In particular, anion exchangers, such as anion exchange resin, and anion exchangers in the form of fiber or monolith are preferably used as the carrier.

After IPA drying liquid has passed through device for removing dissolved oxygen 5 and after dissolved oxygen has been removed, the IPA drying liquid contains an increased amount of water (IPA concentration is decreased) due to water generated by decomposition of dissolved oxygen and due to water that flows out of hydrogen-occluding metal catalyst 51. Variation in IPA concentration may influence yields in semiconductor manufacturing that requires highly precise management. In particular, water in IPA may have large influence on yields in the semiconductor drying process that requires a supply of highly pure IPA. Thus, IPA supply apparatus 1 has water removing device 6 that removes water, which is generated in device for removing dissolved oxygen 5, e.g., when dissolved oxygen is removed. Water removing device 6 is positioned downstream of device for removing dissolved oxygen 5. Water removing device 6 removes water contained in IPA from which dissolved oxygen is removed.

Water removing device 6 is preferably provided with a dehydrating film, but is not limited to this. Water in IPA drying liquid that has passed through device for removing dissolved oxygen 5 is preferably removed by the PV (Pervaporation) method or the VP (Vapor Permeation) method. The dehydrating film may be, for example, a permeable membrane module. The membrane may be made of polymeric material, such as polyimide system, cellulose system and polyvinyl alcohol system, or may be made of inorganic material, such as zeolite. The membrane may preferably be made of zeolite from viewpoint of mechanical strength, dehydrating performance etc.

Liquid that is obtained in device for removing dissolved oxygen 5 flows through water removing device 6, positioned downstream of device for removing dissolved oxygen 5, only when the water concentration in IPA drying liquid exceeds a predetermined value (when IPA concentration in IPA drying liquid is less than the predetermined value). Specifically, only in the above specific case, water in IPA drying liquid is removed and the water concentration (IPA concentration) in IPA drying liquid is adjusted. For this purpose, IPA supply apparatus 1 has alcohol concentration measuring device 7 (alcohol concentration meter) that measures IPA concentration in the liquid obtained by device for removing dissolved oxygen 5 and has bypass line 8 that bypasses water removing device 6. Alcohol concentration measuring device 7 is positioned downstream of device for removing dissolved oxygen 5 (between device for removing dissolved oxygen 5 and water removing device 6). Bypass line 8 branches from IPA supply line 3, bypasses water removing device 6 and merges with IPA supply line 3 again.

When water concentration in IPA drying liquid that has passed through device for removing dissolved oxygen 5 and that is measured by alcohol concentration measuring device 7, exceeds the predetermine value (when IPA concentration in IPA drying liquid is less than the predetermine value), the liquid obtained by device for removing dissolved oxygen 5 is fed through water removing device 6. The liquid is supplied to semiconductor device manufacturing apparatus 101 after the IPA concentration in the liquid is adjusted within a predetermined range. When water concentration in the IPA drying liquid that has passed through device for removing dissolved oxygen 5 is equal to or less than the predetermine value (when IPA concentration in the IPA drying liquid is equal to or more than the predetermine value), the liquid that is obtained by device for removing dissolved oxygen 5 is fed through bypass line 8, which is provided in parallel with water removing device 6, and is then supplied to semiconductor device manufacturing apparatus 101. Control means 19 for bypass line 8 has valves 91, 92 on bypass line 8 and IPA supply line 3 respectively, and a control unit (not shown) that controls valves 91, 92 based on the measured IPA concentration.

IPA supply apparatus 1 has hydrogen adding device 9 that allows hydrogen-occluding metal catalyst 51 to occlude hydrogen. Hydrogen that is occluded in the catalyst reacts with dissolved oxygen in IPA drying liquid and generates water by bringing IPA drying liquid that contains dissolved oxygen into contact with hydrogen-occluding metal catalyst 51, whereby the hydrogen occluded in hydrogen-occluding metal catalyst 51 decreases. Therefore, an additional amount of hydrogen is added to hydrogen-occluding metal catalyst 51, in which hydrogen has been consumed, in order to allow the catalyst to re-occlude hydrogen. In this manner, the catalyst can be effectively utilized.

Hydrogen may be added in various ways. For example, hydrogen gas may be added to IPA drying liquid at an upstream point of hydrogen-occluding metal catalyst 51 (device for removing dissolved oxygen 5) (between device for removing dissolved oxygen 5 and IPA storage tank 2) via a gas dissolving membrane (not shown). Alternatively, the catalyst may be regenerated by means of hydrogen water or hydrogen gas. In the former method, hydrogen is added to the IPA drying liquid, and in the latter method, hydrogen is directly added to hydrogen-occluding metal catalyst 51. In both methods, hydrogen is occluded in hydrogen-occluding metal catalyst 51 at the same time as IPA is brought into contact with hydrogen-occluding metal catalyst 51.

Return line 4 is provided with IPA purifying device 10 in order to remove impurities contained in IPA drying liquid that is discharged from semiconductor device manufacturing apparatus 101 and to purify the IPA drying liquid. IPA purifying device 10 may also be provided between device for removing dissolved oxygen 5 and water removing device 6 or between water removing device 6 and semiconductor device manufacturing apparatus 101. IPA purifying device 10 may preferably be ion exchange resins or an ion adsorbing membrane when metal and ion mainly need to be removed. IPA purifying device 10 may preferably be a filter (microfiltration membrane filter) when fine particles mainly need to be removed.

Second Embodiment

Figure 2:
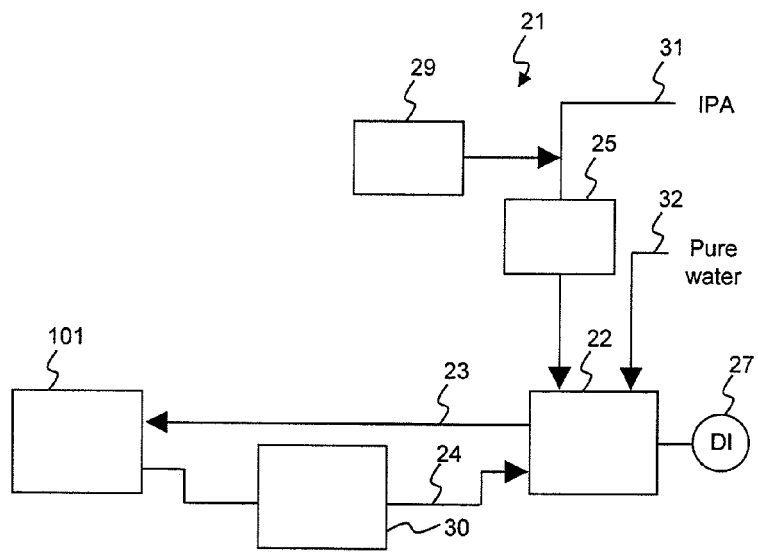
FIG. 2 is a diagram schematically illustrating the arrangement of a rinsing liquid supply apparatus according to a second embodiment of the present invention.

FIG. 2 shows a diagram schematically illustrating the arrangement of a rinsing liquid supply apparatus according to the second embodiment of the present invention.

Rinsing liquid supply apparatus 21 according to the embodiment mixes IPA with pure water, generates rinsing liquid and supplies the rinsing liquid to semiconductor device manufacturing apparatus 101.

Rinsing liquid supply apparatus 21 has mixed water storage tank 22, IPA supply line 31 (alcohol supply means), pure water supply line 32 (pure water supply means), rinsing liquid supply line 23 and return line 24. Mixed water storage tank 22 mixes IPA with pure water in order to generate and store rinsing liquid having a predetermined IPA concentration. IPA supply line 31 supplies IPA to mixed water storage tank 22. Pure water supply line 32 supplies pure water to mixed water storage tank 22. Rinsing liquid supply line 23 feeds the rinsing liquid to semiconductor device manufacturing apparatus 101. Return line 24 feeds the rinsing liquid discharged from semiconductor device manufacturing apparatus 101 back to mixed water storage tank 22. IPA supply line 31 is provided with device for removing dissolved oxygen 25 that removes dissolved oxygen in IPA. Mixed water storage tank 22 is positioned downstream of device for removing dissolved oxygen 25 and pure water supply line 32. Mixed water storage tank 22 stores a mixture of IPA, obtained by device for removing dissolved oxygen 25, and pure water supplied from pure water supply line 32. Mixed water storage tank 22 has alcohol concentration measuring device 27 (alcohol concentration meter) that measures IPA concentration. Rinsing liquid supply apparatus 21 according to the embodiment has a wide applicability not only for rinsing of semiconductor devices but also for cases where a mixture of IPA and pure water is used either, to rinse or to dry an object, or to rinse and to dry an object.

Device for removing dissolved oxygen 25 has the same configuration as device for removing dissolved oxygen 5 according to the first embodiment. The form, material and working principle of hydrogen-occluding metal may also be the same as those of device for removing dissolved oxygen 5 according to the first embodiment.

After IPA has passed through device for removing dissolved oxygen 25 and dissolved oxygen has been removed, the IPA contains an increased amount of water due to water generated by decomposition of dissolved oxygen and due to water that flows out of the catalyst. Accordingly, a water removing device (not shown) that is the same as in the first embodiment may be provided.

Hydrogen adding device 29 and rinsing liquid purifying device 30 may also be provided in the same manner as the first embodiment. These devices may be configured and operated in the same manner as hydrogen adding device 9 and IPA purifying device 10 according to the first embodiment.

Third Embodiment

Figure 3:
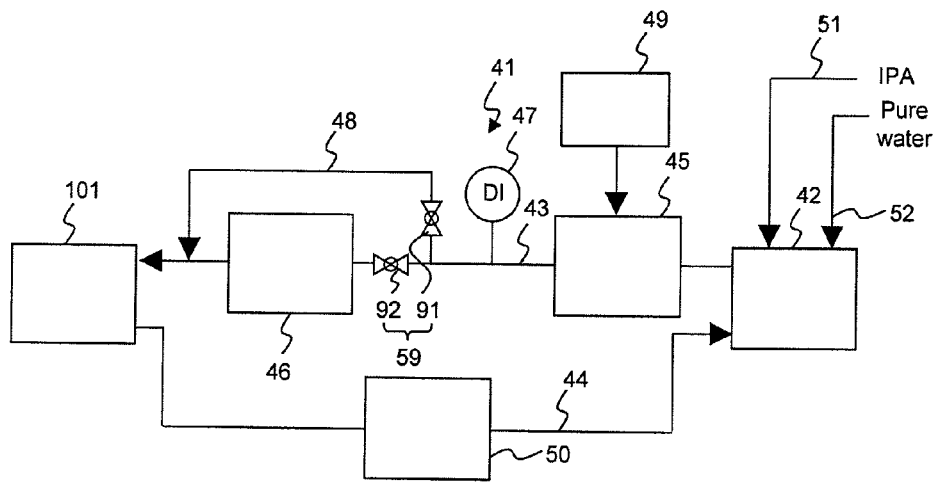
FIG. 3 is a diagram schematically illustrating the arrangement of a rinsing liquid supply apparatus according to a third embodiment of the present invention.

FIG. 3 shows a diagram schematically illustrating the arrangement of a rinsing liquid supply apparatus according to the third embodiment of the present invention.

Rinsing liquid supply apparatus 41 according to the embodiment mixes IPA with pure water, generates rinsing liquid and supplies the rinsing liquid to semiconductor device manufacturing apparatus 101.

Rinsing liquid supply apparatus 41 has mixed water storage tank 42, IPA supply line 51 (alcohol supply means), pure water supply line 52 (pure water supply means), rinsing liquid supply line 43 and return line 44. Mixed water storage tank 42 mixes IPA with pure water in order to generate and store rinsing liquid having a predetermined IPA concentration. IPA supply line 51 supplies IPA to mixed water storage tank 42. Pure water supply line 52 supplies pure water to mixed water storage tank 42. Rinsing liquid supply line 43 feeds the rinsing liquid to semiconductor device manufacturing apparatus 101. Return line 44 feeds the rinsing liquid discharged from semiconductor device manufacturing apparatus 101 back to mixed water storage tank 42. Rinsing liquid supply line 43 is provided with device for removing dissolved oxygen 45 that removes dissolved oxygen in the rinsing liquid and with water removing device 46 positioned downstream thereof. Mixed water storage tank 42 is positioned downstream of IPA supply line 51 and pure water supply line 52. Mixed water storage tank 42 stores a mixture of IPA supplied from IPA supply line 51 and pure water supplied from pure water supply line 52. Device for removing dissolved oxygen 45 is positioned downstream of mixed water storage tank 42. Rinsing liquid supply apparatus 41 according to the embodiment has a wide applicability not only for rinsing semiconductor devices but also for cases where a mixture of IPA and pure water is used either, to rinse or to dry an object, or to rinse and to dry an object.

Device for removing dissolved oxygen 45 has the same configuration as device for removing dissolved oxygen 5 according to the first embodiment. The form, material and working principle of hydrogen-occluding metal may also be the same as those of device for removing dissolved oxygen 5 according to the first embodiment.

After IPA has passed through device for removing dissolved oxygen 45 and dissolved oxygen has been removed, the IPA contains an increased amount of water due to water generated by decomposition of dissolved oxygen and due to water that flows out of the catalyst. When a mixture of IPA and pure water is used for rinsing, various solutions, ranging from a low concentration solution having an IPA concentration of about 2-3% to a relatively high concentration solution having an IPA concentration of about 50%, are used. In particular, removal of water may be required when a high concentration solution is used. Accordingly, water removing device 46 that is the same as in the first embodiment may be provided.

Alcohol concentration measuring device 47, bypass line 48, control means 59 for bypass line 48, hydrogen adding device 49 and rinsing liquid purifying device 50 may also be provided in the same manner as the first embodiment. These devices may be configured and operated in the same manner as alcohol concentration measuring device 7, bypass line 8, control means 19 for bypass line 8, hydrogen adding device 9 and IPA purifying device 10 of the first embodiment. Hydrogen adding device 49 is directly connected to device for removing dissolved oxygen 45 in this embodiment. Alternatively, hydrogen adding device 49 may be provided on IPA supply line 51 or pure water supply line 52 or between mixed water storage tank 42 and device for removing dissolved oxygen 45. IPA purifying device 50 may also be provided on rinsing liquid supply line 43. Device for removing dissolved oxygen 45 and water removing device 46 may also be provided on return line 44 or may be provided on rinsing liquid supply line 43 and on return line 44, respectively.

Example 1

Figure 4:
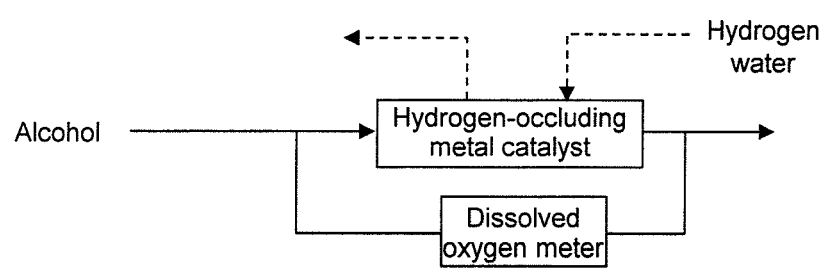
FIG. 4 is a diagram schematically illustrating the arrangement of an apparatus used in Example 1.

An IPA solution having an IPA concentration of 5% was fed through the device shown in FIG. 4 at a flow rate of 100 mL/min. A hydrogen-occluding metal catalyst, in which palladium (nanoparticles) was carried on anion exchangers, was used. Saturated hydrogen water was fed through the hydrogen-occluding metal catalyst in advance so that a sufficient amount of hydrogen was occluded. Thereafter, the 5% IPA solution was fed through the hydrogen-occluding metal catalyst.

Table 1 shows the concentration of the dissolved oxygen in the 5% IPA solution before and after it was fed through the hydrogen-occluding metal catalyst. The concentration of the dissolved oxygen was measured by means of a dissolved oxygen meter ((manufacture of ORBISPHERE, Model 3600). The concentration of the dissolved oxygen was 1.3 ppm before the solution was fed through the hydrogen-occluding metal catalyst. On the other hand, the concentration of the dissolved oxygen was reduced to 8.0 ppb after it was fed through the hydrogen-occluding metal catalyst. The IPA concentration was measured by means of an alcohol concentration meter (manufacture of ATAGO, PR-60PA) before and after the solution was fed through the hydrogen-occluding metal catalyst. The IPA concentration was 5.1% before the solution was fed through the hydrogen-occluding metal catalyst whereas it was 5.0% after the solution was fed through the hydrogen-occluding metal catalyst.

Example 2

Figure 5:
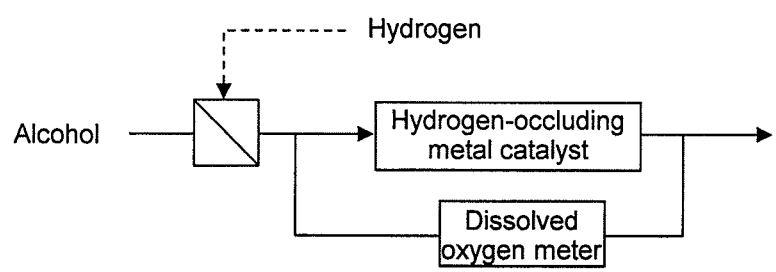
FIG. 5 is a diagram schematically illustrating the arrangement of an apparatus used in Example 2.

An IPA solution having an IPA concentration of 6% was fed through the device shown in FIG. 5 at a flow rate of 100 mL/min. Hydrogen was dissolved in the 6% IPA solution by means of a gas-dissolving membrane, and thereafter the 6% IPA solution was fed through a hydrogen-occluding metal catalyst. A hydrogen-occluding metal catalyst, in which palladium (nanoparticles) was carried on anion exchangers, was used.

Table 1 shows the concentration of the dissolved oxygen in the 6% IPA solution before and after it was fed through the hydrogen-occluding metal catalyst. The concentration of the dissolved oxygen was measured by means of a dissolved oxygen meter (manufacture of ORBISPHERE, Model 3600). The concentration of the dissolved oxygen was 3.3 ppm before the solution was fed through the hydrogen-occluding metal catalyst. On the other hand, the concentration of the dissolved oxygen was reduced to 4.6 ppb after it was fed through the hydrogen-occluding metal catalyst. The IPA concentration was measured by means of an alcohol concentration meter (manufacture of ATAGO, PR-60PA) before and after the solution was fed through the hydrogen-occluding metal catalyst. The IPA concentration was 6.4% before the solution was fed through the hydrogen-occluding metal catalyst whereas it was 6.2% after the solution was fed through the hydrogen-occluding metal catalyst.

TABLE 1

|  | Example 1 | Example 2 |
| --- | --- | --- |
| Before the solution was fed through the hydrogen-occluding metal catalyst | 1.3 ppm | 3.3 ppm |
| After the solution was fed through the hydrogen-occluding metal catalyst | 8.0 ppb | 4.6 ppb |

DESCRIPTION OF REFERENCE NUMERALS

1 IPA supply apparatus
2 IPA storage tank
5, 25, 45 Device for removing dissolved oxygen
6, 46 Water removing device
7, 27, 47 Alcohol concentration measuring device
8, 48 Bypass line
9, 29, 49 Hydrogen adding device
10, 30, 50 IPA purifying device
21, 41 Rinsing liquid supply apparatus
22, 42 Mixed water storage tank
51 Hydrogen-occluding metal catalyst
101 Semiconductor device manufacturing apparatus

The invention claimed is:

1. An alcohol supply apparatus for supplying alcohol, the alcohol being used to rinse or dry an object, or to rinse and to dry an object, and the alcohol supply apparatus comprising:
   a device for removing dissolved oxygen in alcohol, and
   a water removing device positioned downstream of the device for removing dissolved oxygen, wherein the water removing device removes water generated in the device for removing dissolved oxygen when the dissolved oxygen is removed, and
   wherein the device comprises a housing and hydrogen-occluding metal catalyst that is charged in the housing, and
   wherein the hydrogen-occluding metal catalyst has anion exchangers and palladium or platinum carried on the anion exchangers, and the hydrogen-occluding metal catalyst has occluded hydrogen.

2. The alcohol supply apparatus according to claim 1, further comprising:
   an alcohol concentration measuring device for measuring alcohol concentration in a liquid, the liquid being obtained by the device for removing dissolved oxygen,
   a bypass line that bypasses the water removing device,
   a controller that controls the bypass line such that the liquid obtained by the device for removing dissolved oxygen flows through the bypass line when the alcohol concentration, measured by the alcohol concentration measuring device, is equal to or more than a predetermined value and such that the liquid obtained by the device for removing dissolved oxygen flows through the water removing device when the alcohol concentration, measured by the alcohol concentration measuring device, is less than the predetermined value.

3. A rinsing liquid supply apparatus, the rinsing liquid being used to rinse an object, and the rinsing liquid supply apparatus comprising:
   a device for removing dissolved oxygen in alcohol,
   pure water supply,
   a mixed water storage tank positioned downstream of the device for removing dissolved oxygen and the pure water supply, the mixed water storage tank storing a mixture of the alcohol obtained by the device for removing dissolved oxygen and pure water supplied from the pure water supply, and
   wherein the device for removing dissolved oxygen comprises a housing and hydrogen-occluding metal catalyst that is charged in the housing, wherein the hydrogen-occluding metal catalyst has anion exchangers and palladium or platinum carried on the anion exchangers, and the hydrogen-occluding metal catalyst has occluded hydrogen.

4. A rinsing liquid supply apparatus, the rinsing liquid being used to rinse an object, and the rinsing liquid supply apparatus comprising:
   an alcohol supply,
   a pure water supply,
   a mixed water storage tank positioned downstream of the alcohol supply and the pure water supply, the mixed water storage tank storing a mixture of alcohol supplied from the alcohol supply and pure water supplied from the pure water supply, and
   a device for removing dissolved oxygen in alcohol, the device being positioned downstream of the mixed water storage tank], and
   wherein the device for removing dissolved oxygen comprises a housing and hydrogen-occluding metal catalyst that is charged in the housing, wherein the hydrogen-occluding metal catalyst has anion exchangers and palladium or platinum carried on the anion exchangers, and the hydrogen-occluding metal catalyst has occluded hydrogen.

5. A method of supplying alcohol, the alcohol being used to rinse or dry an object, or to rinse and dry an object, comprising:
   removing dissolved oxygen from the alcohol by bringing the alcohol into contact with a hydrogen-occluding metal catalyst which has occluded hydrogen and
   thereafter removing water that is generated when the dissolved oxygen is removed.

6. The alcohol supply apparatus according to claim 1, further comprising a hydrogen adding device that allows the hydrogen-occluding metal catalyst to occlude hydrogen.

7. The alcohol supply apparatus according to claim 1, wherein the water removing device comprises a dehydrating film.

\* \* \* \* \*